United States Patent [19]

Kaplan et al.

[11] Patent Number: 4,668,446
[45] Date of Patent: May 26, 1987

[54] PROCESS FOR MAKING SOFT CONTACT AND INTRAOCULAR LENSES WITH AN ESTERIFIABLE CARBOXYL-CONTAINING POLYMER

[75] Inventors: David G. Kaplan, Encino; Said Pazirandeh, Monrovia; Mario M. Alvarado, Glendora; Lucien Attal, Anaheim, all of Calif.

[73] Assignee: Cilco, Inc., Bellevue, Wash.

[21] Appl. No.: 781,228

[22] Filed: Sep. 27, 1985

[51] Int. Cl.$^4$ .............................................. B29D 11/00
[52] U.S. Cl. ...................................... 264/1.7; 264/2.6; 264/249; 264/274; 351/160 H; 523/106; 525/937; 623/6
[58] Field of Search .................. 264/2.6, 1.7, 2.7, 1.1, 264/249, 274; 525/937; 524/916; 523/106; 604/895; 623/6; 351/160 H

[56] References Cited

U.S. PATENT DOCUMENTS

| | | | |
|---|---|---|---|
| 3,758,448 | 9/1973 | Stamberger | 351/160 H |
| 3,822,089 | 7/1974 | Wichterle | 264/2.6 |
| 3,850,892 | 11/1974 | Shen et al. | 525/340 |
| 3,876,581 | 4/1975 | Neogi | 523/106 |
| 3,880,818 | 4/1975 | Shen et al. | 351/160 R |
| 3,937,680 | 2/1976 | de Carle | 264/2.6 |
| 4,150,471 | 4/1979 | Richardo et al. | 264/1.7 |
| 4,307,043 | 12/1981 | Chase et al. | 264/1.7 |

OTHER PUBLICATIONS

Groggins, P. H., Unit Processes in Organic Synthesis, 4th ed., pp. 609–616, (McGraw-Hill, 1952).

Primary Examiner—James Lowe
Attorney, Agent, or Firm—Pravel, Gambrell, Hewitt & Kimball

[57] ABSTRACT

A process of making soft lenses from an esterifiable, partially cross-linked carboxyl-containing polymer, and a method of attaching a haptic to a swellable intraocular lens. The soft contact lenses are made by first forming a lens button from a hard polymer containing $\alpha,\beta$-ethylenically unsaturated carboxylic acid such as acrylic or methacrylic acid and 0.1–10 mols per 100 mols of monomer of a divinyl cross-linking agent such as 1,4-butanediol dimethacrylate. The hard lens button is then esterified by contact with an alcohol having up to 15 carbon atoms such as n-butanol under esterifying conditions in the substantial absence of water while simultaneously removing water of reaction. Unreacted alcohol may be removed by solvent exchange with a lower molecular weight alcohol and/or drying. In the haptic attachment method, a lens is formed from a polymer and a peripheral bore is formed in the lens; the lens is swollen with an organic fluid such as ethanol and an enlarged end of a haptic is inserted in the peripheral bore; and the organic fluid is then removed from the lens so that the haptic is secured to the lens by contraction of the peripheral bore about the enlarged section of the haptic.

37 Claims, 2 Drawing Figures

PROCESS FOR MAKING SOFT CONTACT AND INTRAOCULAR LENSES WITH AN ESTERIFIABLE CARBOXYL-CONTAINING POLYMER

FIELD OF THE INVENTION

This invention relates to a novel process for making soft lenses with an acrylic type polymer, and particularly to such a process in which acrylic acid type polymer is softened by esterification. The invention also relates to a method of attaching haptics to lenses made of polymers which are swellable by an organic fluid.

BACKGROUND OF THE INVENTION

It is known from U.S. Pat. Nos. 3,850,892 and 3,880,818 to make soft lenses by esterifying acrylic-type polymers, either by direct esterification in which an alcohol is reacted with the pendant carboxyl groups in the polymer, or by indirect esterification in which acid halide is reacted with the pendant carboxyl groups in the polymer, and also by transesterification in which an alcohol is reacted with pendant alkyl carboxylate groups in the polymer to obtain higher alkyl carboxylate groups.

One problem heretofore associated with such lenses is that the direct esterification method as set forth in the aforementioned patents produces lenses which crumble easily or have poor mechanical strength. Moreover, these lenses made by the direct esterification method according to the prior art are generally opaque or become opaque upon exposure to an aqueous environment. Such lenses are generally unsuitable for use as contact lenses or intraocular lenses.

Still another problem with the prior art method of making lenses of esterified acrylic-type polymers is that higher molecular weight alcohols, which are desirable from the standpoint of their ability to soften the lens material, cannot generally be substantially removed by evaporation.

To make intraocular lenses from a process incorporating the method of the aforementioned patents, there has heretofore been no method of which Applicants are aware to securely attach loops, or haptics, to the lenses without damaging the lenses or the haptics. For example, in one heretofore known method of heat stake welding, a haptic made of a material such as polypropylene or polymethylmethacrylate is inserted into a peripheral bore formed in the lens and welded to the lens by inserting hot filaments transversely into the lens material adjacent the peripheral bore. When the heat stake welding procedure is used with lenses made of the soft esterified acrylic-type polymer, the loops are not generally welded adequately in place, the soft lens material is in general deformed, and quite frequently a hole is formed through the lens in the principal area of the heat stake weld.

The present invention provides a method for making soft contact or intraocular lenses which avoids the above deficiencies in the prior art.

SUMMARY OF THE INVENTION

In one aspect, it has been discovered that the poor mechanical strength and opacity of soft lenses made by the prior art direct esterification method is avoided by substantially excluding and removing water from the polymer during the direct esterification thereof with an alcohol. The present invention provides a process for making soft contact or intraocular lenses by direct esterification of an acrylic acid type polymer with an alcohol in such a manner that water is substantially excluded from the polymer, thereby avoiding opacity and lack of mechanical integrity which otherwise results when a substantial quantity of water is present in the esterification media. Broadly, the process comprises the steps of: (a) forming a lens from a hard, solid polymer obtained by polymerizing polymerizable components including at least one monomer selected from the group consisting of $\alpha,\beta$-ethylenically unsaturated carboxylic acids, the polymerizable components containing from about 0.1 to about 10 mols of cross-linking agent per 100 mols of the polymerizable components, the polymer containing at least 10 weight percent of pendant carboxyl groups; and (b) esterifying the pendant carboxyl groups by contacting the hard lens with an alcohol having up to 15 carbon atoms in the substantial absence of water for a time sufficient and under conditions to effect esterification while simultaneously removing water of reaction from the alcohol.

It has also been discovered that when the esterification media includes alcohol having at least 3 carbon atoms, the lens made of the esterified acrylic-type polymer retains a significant quantity of the unreacted alcohol which is not substantially removed by evaporation. The present invention provides a process for removing the unreacted alcohol. The process includes the step of extracting unreacted alcohol having 3 or more carbon atoms from the esterified polymer with a low boiling solvent miscible with the alcohol and substantially nonreactive with the esterified polymer. Upon subsequent removal of the low boiling solvent from the esterified polymer by evaporation, it has been discovered the lens does not become opaque upon exposure to aqueous media and has improved mechanical strength.

In another aspect, the invention provides a novel method of attaching a haptic to a lens without damaging the lens. Broadly, the method includes the steps of: (a) forming a lens from a polymer swellable by an organic fluid, such as, for example, esterified acrylic type polymer; (b) forming a peripheral bore in the lens; (c) swelling the lens with an organic fluid; (d) inserting an end of a haptic into the peripheral bore of the swollen lens, the end having an enlarged transverse cross-sectional portion; and (e) removing the organic fluid from the lens to cause the lens to contract, whereby the haptic is secured to the lens by contraction of the peripheral bore about the enlarged portion of the end of the haptic.

DESCRIPTION OF THE PREFERRED EMBODIMENTS

Figure 1:
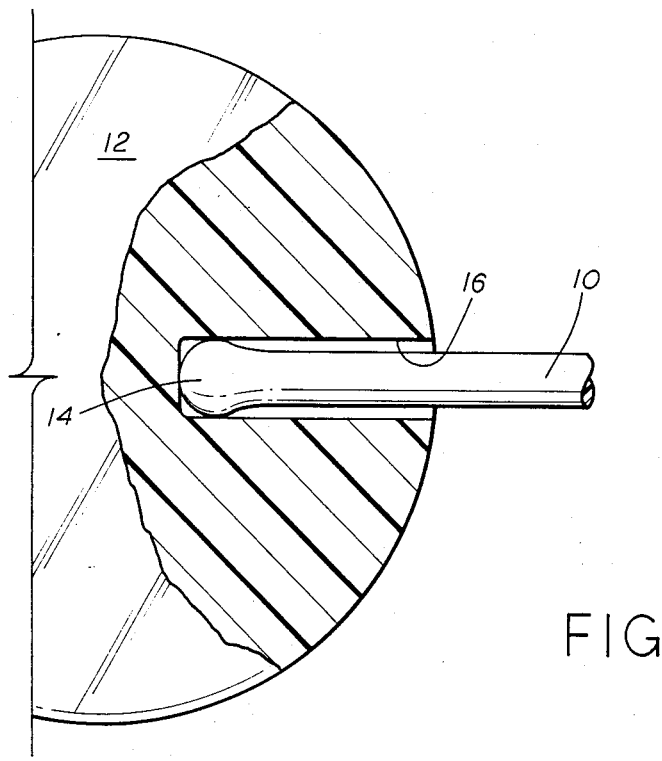
FIG. 1 is a sectional illustration of a portion of a swollen lens with a haptic inserted in the peripheral bore formed in the lens according to the method of the present invention.

As summarized above, the present process for making soft contact or intraocular lenses has two essential steps. First, a lens is formed from a hard, solid acrylic acid type polymer. Second, the pendant carboxyl groups in the lens are esterified with alcohol in such manner that the water of reaction is essentially removed from the lens material. The method of direct esterification is generally set forth in U.S. Pat. No. 3,880,818 and U.S. Pat. No. 3,850,892, which are hereby incorporated by reference, except that these patents do not address the poor mechanical strength and opacity of lenses made by the direct esterification process as described therein, nor suggest that the opacity and mechanical strength problems can be avoided by an exclusion of water from the direct esterification media.

In the first essential step of the method, a lens is formed by conventional molding and/or machining techniques from an acrylic acid type polymer. The acrylic acid type polymer is obtained by conventional polymerization methods and techniques well known in the art. In general, the polymer is obtained by polymerizing one or more monomers including an $\alpha,\beta$-ethylenically unsaturated carboxylic acid and a cross-linking agent with di-ethylenic unsaturation. Suitable unsaturated carboxylic acid monomers include monomers having the general formula $$\begin{array}{ccc} R_1 & R_3 & O \\ | & | & \| \\ C=C-C-OH \\ | \\ R_2 \end{array}$$

wherein $R_1$ and $R_2$ are independently hydrogen or alkyl groups having up to 6 carbon atoms and $R_3$ is hydrogen or methyl. Specific representative examples of suitable carboxylic acid monomers include acrylic acid, methacrylic acid, 1-butenoic acid, isopentene-2-oic acid, 2,3-dimethylbutene-2-oic acid, 2-methylpentene-2-oic acid, tiglic acid, angelic acid, senecioic acid, maleic acid, itaconic acid, and the like. Of these, acrylic acid is preferred.

The cross-linking agent must be present in the monomer mixture in an amount at least sufficient to provide satisfactory dimensional stability, but not so great an amount that the resulting polymer cannot be converted to a flexible and physiologically compatible composition by direct esterification. Satisfactory polymers are generally obtained from a monomer mixture containing from about 0.1 to about 10 mols, preferably 1 to 3 mols, of the cross-linking agent per 100 mols of the monomer mixture.

Suitable cross-linking agents include in general any organic di-ethylenically unsaturated monomer. Representative suitable cross-linking agents include: divinyl esters of organic dicarboxylic acids such oxalic, terephthalic, hexahydroterephthalic, malonic, succinic, and the like; divinyl ethers such as vinyl ether, dibut-3-enyl ether, dipent-4-enyl ether, and the like; divinyl hydrocarbons such as divinyl benzene, divinyl toluene, 1,4-pentadiene, 1,5-hexadiene, and the like; and aliphatic diol esters of $\alpha,\beta$-ethylenically unsaturated carboxylic acids such as for example 1,4-cyclohexanediol diacrylate and dimethacrylate, and the corresponding esters of 1,3-propanediol, 1,2-propanediol, 1,4-butanediol, ethylene glycol, and the like. Of these, the aliphatic diol diacrylate and dimethacrylate esters are preferred.

The monomer mixture from which the hard acrylic acid type polymer is prepared may further include esters and anhydrides of $\alpha,\beta$-ethylenically unsaturated carboxylic acids. Suitable esters include the alkyl, hydroxyalkyl and alkoxyalkyl esters of the $\alpha,\beta$-ethylenically unsaturated carboxylic acids in which the alkyl, hydroxyalkyl or alkoxyalkyl substituent may have up to about 11 carbon atoms. Such esters generally conform to the formula $$\begin{array}{ccc} R_1 & R_3 & O \\ | & | & \| \\ C=C-C-OZ \\ | \\ R_2 \end{array}$$

wherein $R_1$, $R_2$ and $R_3$ are as specified above and Z is an alkyl, hydroxyalkyl, or alkoxyalkyl group having up to about 11 carbon atoms. Specific representative examples of suitable esters include the methyl, ethyl, n-propyl, i-propyl, and butyl acrylates and methacrylates; 2-hydroxyethyl acrylate and methacrylate, 2-hydroxypropyl acrylate and methacrylate, and the like.

The content of the unsaturated carboxylic acid in the monomer mixture should be sufficient to provide a polymer with at least 10 wt. % of carboxyl group substituents. Preferably, the monomer mixture from which the hard polymer is obtained contains, per 100 mols of the monomer mixture: from about 10 to about 90 mols, more preferably 20 to 40 mols, of the $\alpha,\beta$-ethylenically unsaturated carboxylic acid; from about 10 to about 90 mols, more preferably 60 to 80 mols, of the ester of the $\alpha,\beta$-ethylenically unsaturated carboxylic acid; and from about 0.1 to about 10 mols, more preferably 1 to 3 mols, of the di-ethylenically unsaturated cross-linking agent.

If desired, the polymer may contain minor amounts of various additives conventional in the art. For example, mold release compounds or processing additives such as lecithin may be added which may or may not remain in the polymer following esterification. Other additives which may be desired to remain in the esterified polymer, such as UV absorbers or dyes, should be properly selected so that they are not removed or chemically altered during esterification of the polymer and any subsequent processing. Such additives may, for example, be covalently bonded to the polymer so that they are not removed.

The foregoing monomers may be polymerized by a catalyst such as a peroxide or actinic light, or by the use of heat and pressure. Such polymers, their method of preparation, and the method of forming lenses therefrom are well known in the art.

The lenses made of the hard acrylic acid type polymer may be, and preferably are, polished by conventional techniques and procedures before subsequent esterification. Where the polishing includes contacting the lenses with an aqueous media, such as, for example, in polishing the lenses with an aqueous slurry of glass beads, the lenses should be thoroughly dried before esterification. The drying is usually effected by placing the lenses in an oven at suitable elevated temperatures, generally up to about 60° C., for a period of time, generally about 8 to 72 hours, to substantially remove any water from the polymer.

In the second essential step of the process, the lenses formed from the hard polymer are esterified with an alcohol in such a manner that the esterification media is substantially free of water. Alcohols suitable for esterification generally contain up to about 15 carbon atoms. Preferably the alcohol used has 3 to 7 carbon atoms. Alcohols having fewer than 3 carbon atoms are less effective in softening the lens, while with alcohols having more than 7 carbon atoms it is more difficult to achieve adequate esterification because of their relatively poor ability to diffuse into the interior of the hard polymer material.

Esterification is in general effected by placing the lens formed from the hard material in the liquid alcohol at an elevated temperature, preferably from about 50° C. to about 200° C., optionally in the presence of an esterification catalyst, such as a soluble acid, preferably sulfuric acid, in a concentration of from about 0.2 to about 5 percent by weight of the alcohol.

An essential feature of the present process is that the esterification is in the substantial absence of water and involves simultaneously removing water of reaction from the alcohol. Preferably, the removal of the water of reaction is accomplished by refluxing the esterification alcohol and removing aqueous distillate from the esterification medium. For example, removal of the aqueous distillate is conveniently effected by employing a Dean-Stark reflux apparatus equipped with a condenser, or similar apparatus.

The reaction will in general be carried out at the boiling point of the esterification medium, i.e. at about the normal boiling point of the alcohol. Higher temperatures may be employed by using pressures higher than atmospheric, but will generally be below about 200° C. The reaction is generally completed in from about 1 to about 100 hours, and usually between 10 and 20 hours when an acid catalyst is used. Completion of the esterification reaction is observed, for example, by a marked reduction in the amount of aqueous distillate collected.

Following esterification, the lens is removed from the alcohol. Unreacted alcohol having fewer than 3 carbon atoms and remaining in the polymer matrix following esterification may be removed by drying the lens in a vacuum oven or other suitable equipment at an elevated temperature, generally up to about 80° C., preferably from about 40° C. to about 60° C. The time required to substantially remove the residual alcohol from the lens will depend on the particular alcohol, the type of esterified polymer, lens dimensions, and the drying conditions. At 40°-60° C., for example, removal of the alcohol is substantially complete after about 8 to about 72 hours in a vacuum oven.

It has been found, however, that unreacted alcohol having 3 or more carbon atoms and remaining in the polymer matrix following esterification is not adequately removed by the evaporation step described above, especially from the interior of the lens. Lenses containing unreacted alcohols having 3 or more carbon atoms which are dried in an oven as described above generally have poor mechanical strength which is believed to result from stresses caused by contraction at the surface of the lens due to removal of unreacted alcohol therefrom, while the interior of the lens does not contract because of no substantial removal of alcohol therefrom. Moreover, such lenses containing unreacted alcohol generally eventually become opaque when exposed to aqueous media for a period of time.

It has now been found that the foregoing problems associated with retention of unreacted alcohol having 3 or more carbon atoms are avoided if, prior to the alcohol evaporation step described above, the lens of the esterified polymer is contacted with a low boiling solvent miscible with the alcohol used in the esterification and substantially non-reactive with the esterified polymer. In this manner, a high boiling alcohol such as butanol or pentanol is extracted by the low boiling solvent.

The low boiling solvents which may be used generally include low molecular weight solvents which have a boiling point less than that of the propyl alcohols. Specific representative solvents include, for example, methanol, ethanol, ether and the like. The preferred solvent is ethanol. In addition, a combination of low boiling solvents may be used, and the extraction may be carried out in a plurality of stages using the same or different solvents and/or combination of solvents in subsequent stages.

The extraction is generally performed at a temperature of from about 20° C. to about 100° C., preferably in the range of from about 60° C. to about 80° C. Above about 100° C., the lens may be damaged during the contact with the low boiling solvent, while at temperatures below about 20° C. an unreasonable period of time is generally required for substantial removal of the high boiling alcohol.

The extraction of the high boiling alcohol with the low boiling solvent may be done in any apparatus suitable for this purpose, including, for example, a soxhlet extractor or refluxing apparatus. The apparatus preferably provides continuous agitated contact of the lens with fresh low boiling solvent, i.e. solvent substantially free of the high boiling alcohol.

The contact of the lens with the low boiling, miscible solvent is generally for a period of time sufficient to substantially remove the high boiling alcohol from the lens material. The high boiling alcohol is substantially removed when upon evaporation of the low boiling solvent an inconsequential amount of alcohol remains in the lens so that the lens does not become opaque upon indefinite exposure to an aqueous environment. This period of time is at least 4 hours, but may be anywhere up to about 120 hours or more, and is typically in the range of from about 36 to about 72 hours.

At present, it is not fully understood why esterifying the acrylic acid type polymer in the substantial absence of water results in a lens with mechanical and optical properties suitable for use as a contact or intraocular lens. It is believed that the exclusion of water from the esterification medium may remove water of reaction which would otherwise be trapped in the polymer matrix and not be removed by evaporation of the unreacted alcohol therefrom. The removal of the water from the polymer matrix during esterification may result in improved optical and mechanical properties either because the water is not present in the esterified lens, and/or because the polymer is more completely esterified by the water removal during esterification. It is to be understood, however, that the present invention is not bound or limited by these theories.

When it is desired to manufacture an intraocular lens from the soft esterified lens material, the present invention also provides a method for attaching haptics or loops to the soft lens. Briefly, the method includes the steps of forming a peripheral bore in the lens to which the haptic is to be attached, swelling the lens with an organic fluid, inserting an end of a haptic into the peripheral bore, the end having an enlarged transverse cross-sectional portion, and removing the organic fluid from the lens, thereby contracting the lens, whereby the haptic is secured to the lens by contraction of the peripheral bore about the enlarged portion of the end of the haptic.

While this method is especially well adapted to attach a haptic to a lens made of the soft esterified material according to the process described above, it is also contemplated that the method will be suitable for attaching a haptic to a lens made from any polymer swellable by an organic fluid. The polymer must be cross-linked to an extent sufficient to avoid dissolution of the polymer when an organic liquid is used, although non-crosslinked polymers may be swellable by an organic vapor without being subjected to dimensional instability. The polymer must be swellable by an organic fluid because water cannot generally be used to swell the polymer since it usually adversely affects the optical properties thereof. The organic fluid does not necessarily have to be substantially non-reactive with the lens material, and it is contemplated that in some instances the organic fluid may advantageously modify the properties of the lens material, as well as swell the polymer. For example, an acrylic acid type polymer may be esterified as described above, and swollen at the same time by an alcohol. Polymers contemplated as being suitable for the present method of haptic attachment include, for example, polymethylmethacrylate, polymethylpentene and silicone, in addition to the esterifiable and esterified acrylic-type polymers.

A peripheral bore is formed in the lens of sufficient cross-sectional area to accommodate the haptic. By the adjective "peripheral" is meant that the bore opens to the exterior surface of the lens. The bore may be formed in the lens by drilling, or by any other method for forming bores in lenses which are conventional in the art. The bore may be positioned in the lens as required to provide a desired exit angle. Any number of bores may be formed in the lens if it is desired to attach a plurality of haptics thereto. The bore or bores may be formed after swelling the polymer with the organic fluid, but, because the swollen material is generally softer and thus more difficult to machine, is preferably formed prior to swelling the lens material taking into account the expansion of the bore upon exposure of the lens material to the organic fluid.

The lens is swollen with an organic liquid or vapor generally by exposing it to the fluid for a period of time sufficient to cause swelling and expansion of the lens material. The exposure may be at an elevated temperature to accelerate swelling. Suitable organic fluids will depend on the specific polymer of which the lens is made, but generally include methanol, ethanol, ether and the like, and combinations thereof.

The haptic or loop may be made of any material and have for the portion of the haptic exterior the lens any desired configuration suitable for its intended use. Many physiologically accepted materials and configurations are well known to those skilled in the art. The end of the haptic to be inserted in the peripheral bore may have many different cross-sectional shapes, such as, for example, circular, rectangular, flat, etc., but must have a portion with a cross-section enlarged with respect to the remaining inserted portion of the haptic end. For example, the enlarged portion may be in the shape of a ball, barb, disc, knot, etc. The enlarged portion does not need to be located at the very end of the inserted haptic end, but should be disposed so the enlarged portion is sufficiently embedded in the lens following contraction that the haptic is not easily pulled loose. Generally, the softer the cross-linked polymer, the larger or more exaggerated the enlarged portion of the haptic end should be.

In one preferred embodiment, the haptic is made of a thermoplastic material, such as a polyolefin, for example polypropylene. Such a loop may be provided with an enlarged transverse cross-sectional portion by exposure of the haptic end to be inserted in the bore to a source of heat. For example, with polypropylene loops, it has been found that exposure to a heat source of 360° F. approximately 0.5 inches from the end of the loop for about 1 second causes a loop filament to form a ball at the terminal end thereof as seen in the figures. By duplicating the ball-forming conditions, the resulting ball has a minimal variation in its transverse dimension which is generally within acceptable tolerances. For polypropylene filaments having a 0.15 mm diameter, for example, the aforementioned ball-forming conditions will result in a ball being formed which has a diameter of about 0.22–0.25 mm. For such polypropylene loops, the size of the ball should not exceed about 0.25 mm because sizes larger than this generally result in a fragile ball which may break off.

Following insertion of the haptic end into the peripheral bore of the swollen lens, the organic fluid is removed, preferably by evaporation. The evaporation may be done, for example, in an oven at a temperature and for a time sufficient to remove organic fluid from the polymer so that it contracts sufficiently to hold the haptic in place, generally substantially to its original dimension before swelling with the organic fluid. The contraction of the lens material contracts and compresses the bore about the enlarged portion of the inserted haptic end, securing the haptic to the lens.

Figure 2:
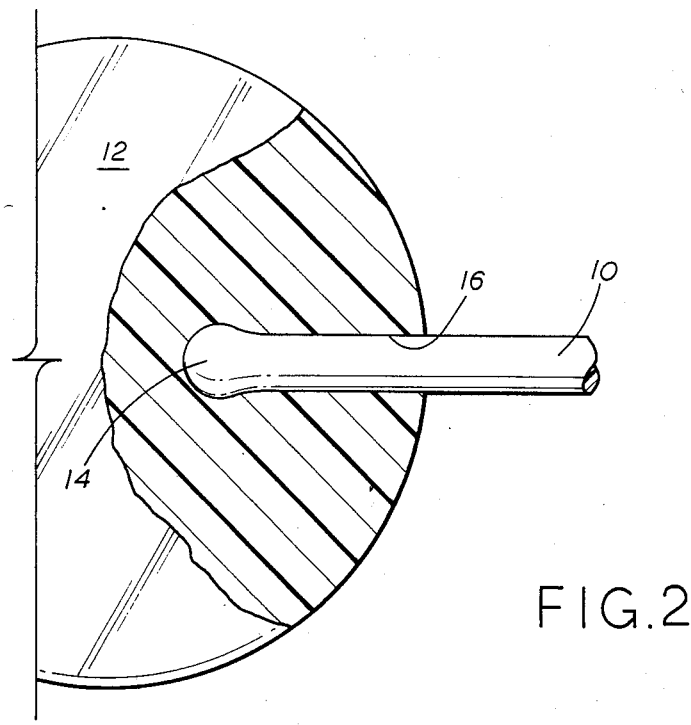
FIG. 2 is an illustration of the portion of the lens and haptic of FIG. 1 following removal of the organic fluid.

Referring now to FIG. 1, the haptic 10 desired to be secured in the lens 12 swollen by an organic fluid has one end which has an enlarged transverse cross-sectional portion 14. The end with the enlarged portion 14 is inserted into the peripheral bore 16 of the lens 12. Then, the organic fluid is removed from the lens, causing the lens 12 to contract. The contraction causes the haptic 10 to be secured to the lens 12 by contraction and compression of the peripheral bore 16 about the enlarged portion of the haptic end 14, as seen in FIG. 2.

In the process described above in which a hard acrylic acid type polymer lens material is softened by esterification, the attachment of the haptic according to the present method may be conveniently achieved following the esterification and extraction of the high boiling alcohol with the low boiling solvent, but before the solvent evaporation step. The peripheral bore may be formed in the lens either before or after esterification, preferably before the esterification. Following the formation of the peripheral bore in the lens and subsequent esterification, the enlarged end of the haptic may be inserted into the bore before the drying step. At this point, the lens is in a swollen condition. When the low boiling solvent is subsequently removed from the lens with the haptic inserted in the peripheral bore, the lens contracts and the peripheral bore compresses around the enlarged end of the haptic, thereby securing the haptic to the lens.

The invention is more fully understood by way of the examples which follow.

EXAMPLE 1

A hard polymer was prepared by polymerizing a mixture of acrylic acid (18 ml), n-butyl methacrylate (95 ml), and 1,4-butanediol dimethacrylate (3.1 ml). The polymerization was effected by adding 0.2g (about 0.5 weight percent) of 2,5-dimethyl-2,5-bis(2-ethylhexoylperoxy)hexane (obtained from Witco Chemical Corp.; hereinafter referred to by its trade designation USP 245). For the polymerization, the mixture was placed in a 30 ml glass test tube. At 60° C., the polymerization was completed in about 4 hours. The product was a hard, clear and inflexible acrylic acid type backbone polymer containing pendant carboxyl groups.

The hard polymer was then cut into lens blanks or buttons in which edge holes for attaching haptics were drilled. The lenses were then tumbled and polished with a slurry of glass beads and water. The polished lens blanks were placed in a vacuum oven at 50° C. for about 12 hours to remove any water which might be present in the polymer. The lens blanks were then placed in a 300 ml flask equipped with a Dean-Stark receiver provided with a reflux overflow return to which a condenser had been added. Two hundred ml n-butanol and 2 ml concentrated $H_2SO_4$ were added to the flask. The mixture was refluxed for 16 hours and water collected in the Dean-Stark receiver. The lenses were removed from the flask, placed in a Soxhlet extractor and washed with ethanol for 72 hours. The lenses were then dried in a vacuum oven at 50° C. for 48 hours. The lenses were soft and flexible, very clear and did not become cloudy upon immersion in water even after about 4 months.

The following Comparative Examples 1–7 are provided to show that the improved mechanical and optical properties of the lenses made according to the present invention are not obtainable by various other modifications of the prior art procedure. In Comparative Example 1, the methods described in U.S. Pat. Nos. 3,850,892 and 3,880,818 were followed to show that useful lenses are not obtained by these methods. In Comparative Example 2, fresh $H_2SO_4$ is used to show that the quality of the esterification catalyst is not sufficient to produce lenses suitable for contact and intraocular use. In Comparative Examples 3A and 3B, different alcohols were used in the esterification step with no improvement. In Comparative Examples 4A and 4B, the extent of cross-linking was varied with no improvement. The drying time was varied with no improvement in Comparative Examples 5A and 5B. In Comparative Example 6, a hydrophilic monomer was used to prepare the hard polymer with no improvement.

COMPARATIVE EXAMPLE 1

A hard polymer was prepared by polymerizing a mixture of 6 ml acrylic acid, 20 ml butyl acrylate, 25 ml butyl methacrylate and 6 ml of ethylene glycol dimethacrylate. The polymerization was effected by the addition of 4 drops of USP 245. For the polymerization, the mixture was placed in a 30 ml glass test tube. The polymerization was completed in about 4 hours at 60° C.

The hard polymer was then cut into lens blanks. The lens blanks were placed in a vacuum oven at 50° C. for about 12 hours. The lens blanks were placed in a 300 ml flask provided with a condenser for refluxing. n-Butanol containing 0.5% by weight concentrated $H_2SO_4$ was added to the flask. The lenses were refluxed for 16 hours. The lenses were removed from the flask and dried in an oven at 50° C. for 16 hours. These lenses crumbled when held in the hand and turned opaque in water.

COMPARATIVE EXAMPLE 2

The procedure of Comparative Example 1 was repeated, but the concentrated sulfuric acid came from a freshly opened bottle of sulfuric acid. The resulting lenses did not crumble when held in the hand, but they did become opaque after a 1 hour submersion in water.

COMPARATIVE EXAMPLE 3A

The procedure of Comparative Example 2 was repeated, but n-pentanol was used in place of butanol. The resulting lenses became opaque in water.

COMPARATIVE EXAMPLE 3B

The procedure of Comparative Example 2 was repeated, but n-octanol was used in place of the butanol. The resulting lenses became opaque in water.

COMPARATIVE EXAMPLE 4A

The procedure of Comparative Example 2 was repeated, but 3 ml of ethylene glycol dimethacrylate was used in the polymerization instead of 6 ml. The resulting lenses became opaque in water.

COMPARATIVE EXAMPLE 4B

The procedure of Comparative Example 2 was repeated, but 9 ml of ethylene glycol dimethacrylate was used in the polymerization instead of 6 ml. The resulting lenses became opaque in water.

COMPARATIVE EXAMPLE 5A

The procedure of Comparative Example 2 was repeated, except that the esterified lens blanks were dried at 50° C. for 4 days in a vacuum oven instead of 16 hours. The resulting lenses became opaque in water.

COMPARATIVE EXAMPLE 5B

The procedure of Comparative Example 2 was repeated, except that the esterified lens blanks were dried at 50° C. for 10 days in a vacuum oven instead of 16 hours. The resulting lenses became opaque in water.

COMPARATIVE EXAMPLE 6

A hard polymer was prepared by polymerizing a mixture of 8.0 ml butyl methacrylate, 6.3 ml hydroxyethyl methacrylate and 0.36 ml 1,4-butanediol diacrylate. The polymerization was effected by the addition of 3 drops of USP 245. For the polymerization, the mixture was placed in a 30 ml glass test tube. The polymerization was completed in about 4 hours at 60° C.

The hard polymer was then cut into lens blanks. The lens blanks were placed in a 300 ml flask provided with a condenser for refluxing. n-Butanol containing 1% by weight concentrated $H_2SO_4$ was added to the flask. The lens blanks were refluxed for 6 hours. The lenses were placed in a vacuum oven and dried.

The resulting lenses turned opaque in water.

COMPARATIVE EXAMPLE 7

A hard polymer was prepared by polymerizing a mixture of 12.8 ml butyl methacrylate, 4.1 ml acrylic acid, and 0.36 ml 1,4-butanediol diacrylate. The polymerization was effected by the addition of 3 drops of USP 245. For the polymerization, the mixture was placed in a 30 ml glass test tube. The polymerization was completed in about 4 hours at 60° C.

The hard polymer was cut into lens blanks. The lens blanks were placed in a 300 ml flask provided with a condenser for refluxing. n-Butanol containing 1% by weight concentrated $H_2SO_4$ was added to the flask. The lens blanks were refluxed for 3 hours. The lenses were placed in a vacuum oven and dried.

The resulting lenses turned opaque in water.

EXAMPLE 2

The procedure of Example 1 was repeated, but with varying cross-linking agent contents, and included attachment of a haptic to the lenses. After the lens blanks were cut, an edge hole was drilled in the lens to a diameter of 0.15 mm. A polypropylene haptic with an attachment end having a diameter of 0.15 mm was placed next to a 360° F. heating element (soldering iron) for 1 second. The loop material shrank back into a small ball at the end of the straight portion of the loop. The ball size was approximately 0.22–0.25 mm. The ball of the loop was inserted into the edge hole immediately following the ethanol wash procedure at which time the diameter of the bore was about 0.20–0.24 mm. Although the bore diameter was slightly less than that of the enlarged end of the haptic, the ethanol-swollen lens was soft enough to allow easy insertion. Finally, the haptic and lens were placed in a vacuum oven at 50° C. for 48 hours.

The attachment of the haptic to the lens was then pull tested. In the pull test, the haptic end away from the lens is attached to a strain gauge such as a Correx Gramm Pond Gauge. Pulling in a direction coincident with the edge hole until the haptic breaks or is pulled from the lens, the highest reading on the gauge is recorded in grams. Generally, a reading of about 40 grams or more is acceptable. Results of the pull testing of lenses of varying monomer content are given in Table I.

TABLE I

| Specimen Lot | Monomer Mixture AA[1]/n-BMA[2] (mol ratio) | BDDMA[3] (mol %) | Esterifying Alcohol | Pull Test[4] (g) |
|---|---|---|---|---|
| 1 | 30/70–10/90 | 2 | n-butanol | 43 |
| 2 | 30/70–10/90 | 6 | n-butanol | 71 |
| 3 | 30/70–20/90 | 10 | n-butanol | 119 |

Notes for Table I:
[1] Acrylic acid.
[2] n-Butylmethacrylate.
[3] 1,4-Butanediol dimethacrylate.
[4] Average of 4 lenses from specimen lot.

The foregoing description of the method of the invention is illustrative and explanatory thereof. Various changes in the materials, apparatus, and particular steps employed will occur to those skilled in the art. It is intended that all such variations within the scope and spirit of the appended claims be embraced thereby.

We claim:

1. A process for making soft contact or intraocular lenses, comprising the steps of:
   (a) forming a lens from a solid polymer obtained by polymerizing polymerizable components including at least one monomer selected from the group consisting of $\alpha,\beta$-ethylenically unsaturated carboxylic acids, said polymerizable components containing from about 0.1 to about 10 mols of di-ethylenically unsaturated cross-linking agent per 100 mols of said polymerizable components, said polymer containing at least 10 weight percent of pendant carboxyl groups; and
   (b) esterifying said pendant carboxyl groups by contacting said lens with a liquid alcohol having up to 15 carbon atoms in the substantial absence of water for a time sufficient and under conditions to effect esterification while simultaneously removing water of reaction from said alcohol.

2. The process of claim 1, wherein said $\alpha,\beta$-ethylenically unsaturated carboxylic acid monomer has the formula

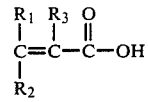

wherein $R_1$ and $R_2$ are independently hydrogen or alkyl groups having up to 6 carbon atoms and $R_3$ is hydrogen or methyl.

3. The process of claim 1, wherein said cross-linking agent is selected from the group consisting of: divinyl esters of dicarboxylic acids, divinyl ethers, divinyl hydrocarbons, aliphatic diol diesters of $\alpha,\beta$-ethylenically unsaturated carboxylic acids, and combinations thereof.

4. The process of claim 1, wherein said polymerizable components include at least one monomer selected from the group consisting of: alkyl, hydroxyalkyl, and alkoxyalkyl esters of $\alpha,\beta$-ethylenically unsaturated carboxylic acids.

5. The process of claim 1, wherein said alcohol has 3 to 7 carbon atoms.

6. The process of claim 1, wherein said esterification step includes removing aqueous distillate from said alcohol during said contact of said lens therewith.

7. A process for making soft contact or intraocular lenses, comprising the steps of:
   (a) forming a lens from a solid polymer obtained by polymerizing polymerizable components comprising, per 100 mols of said components:
      (1) from about 10 to about 90 mols of at least one monomer selected from the group consisting of $\alpha,\beta$-ethylenically unsaturated carboxylic acids having the formula

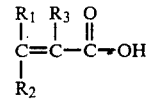

wherein $R_1$ and $R_2$ are independently hydrogen or alkyl groups having up to 6 carbon atoms and $R_3$ is hydrogen or methyl, said acid monomer being present in an amount sufficient for said polymer to contain at least 10 weight percent of pendant carboxyl groups;

(2) from about 10 to about 90 mols of at least one monomer having the formula

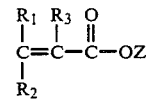

wherein $R_1$ and $R_2$ are independently hydrogen or alkyl groups having up to 6 carbon atoms, $R_3$ is hydrogen or methyl, and Z is an alkyl, hydroxyalkyl or alkoxyalkyl group having up to about 11 carbon atoms; and (3) from about 0.1 to about 10 mols of di-ethylenically unsaturated cross-linking agent selected from the group consisting of: divinyl esters of dicarboxylic acids, divinyl ethers, divinyl hydrocarbons, aliphatic diol diesters of $\alpha,\beta$-ethylenically unsaturated carboxylic acids, and combinations thereof; and (b) esterifying said pendant carboxyl groups by contacting said lens with a substantially water-free alcohol having 3 to 7 carbon atoms for a time sufficient and under conditions to effect esterification, and by simultaneously removing aqueous distillate from said alcohol during said contact.

8. The process of claim 7, wherein said polymerizable components comprise, per 100 mols of said polymerizable components, from about 20 to about 40 mols of said α,β-ethylenically unsaturated carboxylic acid, from about 60 to about 80 mols of said carboxylic acid ester, and from about 1 to about 3 mols of said cross-linking agent.

9. The process of claim 7, wherein said esterification is in the presence of an acid catalyst.

10. The process of claim 1 wherein said alcohol has 3 or more carbon atoms, and further comprising the steps of:

(a) contacting the esterified lens with a low boiling solvent at a temperature of from about 20° C. to about 100° C. for a period of time of at least 4 hours to substantially extract unreacted alcohol having 3 or more carbon atoms from the lens, said solvent being miscible with the unreacted alcohol and substantially non-reactive with the esterified polymer; and (b) removing said low boiling solvent from the lens by evaporation.

11. The process of claim 10, wherein the unreacted alcohol has 3 to 7 carbon atoms and said low boiling solvent comprises methanol, ethanol, ether or a combination thereof.

12. The process of claim 10, wherein said contact is for a period of time of from 4 to about 120 hours.

13. The process of claim 10, wherein said contact is at a temperature from about 60° C. to about 80° C.

14. The process of claim 10, wherein said evaporation is at a temperature less than about 80° C. for a period of time from about 8 to about 72 hours.

15. The process of claim 5, further comprising the steps of:

(a) contacting the esterified lens with liquid methanol, ethanol, ether or a combination thereof for a period of time from about 4 to about 120 hours at a temperature from about 60° C. to about 80° C.; and (b) evaporating said methanol, ethanol, ether or combination thereof from the lens at a temperature less than about 80° C. for a period of time from about 8 to about 72 hours.

16. The process of claim 15, wherein said contact is for a period of time from about 36 to about 72 hours.

17. The process of claim 15, wherein said contact is continuous and agitated with said methanol, ethanol, ether or combination thereof substantially free of the 3 to 7 carbon atom alcohol.

18. A method for attaching a haptic to an intraocular lens, comprising the steps of:

(a) forming a lens from a polymer swellable by an organic fluid;
(b) forming a peripheral bore in said lens;
(c) swelling said lens with an organic fluid;
(d) inserting an end of a haptic into said peripheral bore, said haptic end having a portion of enlarged transverse cross-section; and
(e) removing said organic fluid from said lens and thereby contracting said lens, whereby said haptic is secured to said lens by contraction of said peripheral bore about said enlarged portion.

19. The method of claim 18, wherein said polymer is cross-linked.

20. The method of claim 18, wherein said organic fluid is a liquid.

21. A method for attaching a haptic to an intraocular lens, comprising the steps of:

(a) forming a lens from a cross-linked polymer swellable by an organic liquid;
(b) forming a peripheral bore in said lens;
(c) swelling said lens with an organic liquid;
(d) inserting an end of a haptic into said peripheral bore, said haptic end having a portion of enlarged transverse cross-section; and
(e) removing said organic liquid from said lens and thereby contracting said lens, whereby said haptic is secured to said lens by contraction of said peripheral bore about said enlarged portion.

22. The method of claim 21, wherein said peripheral bore is formed in said lens before said swelling of said lens.

23. The method of claim 21, wherein said cross-linked polymer comprises an acrylic-type polymer.

24. The method of claim 21, wherein said organic liquid comprises methanol, ethanol, ether or a combination thereof.

25. The method of claim 21, wherein said haptic comprises a thermoplastic material and said enlarged portion is a ball formed by exposing said haptic end to heat.

26. A process for making soft contact or intraocular lenses, comprising the steps of:

(a) polymerizing polymerizable components including, per 100 mols of each said components:
(1) from about 10 to about 90 mols of at least one monomer selected from the group consisting of α,β-ethylenically unsaturated carboxylic acids of the formula

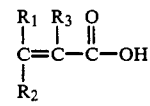

where $R_1$ and $R_2$ are independently hydrogen or alkyl groups having up to 6 carbon atoms and $R_3$ is hydrogen or methyl, said acid monomer being present in an amount sufficient for the resulting polymer to contain at least 10 weight percent of pendant carboxyl groups;

(2) from about 10 to about 90 mols of at least one monomer selected from the group consisting of esters of α,β-ethylenically unsaturated carboxylic acids having the formula

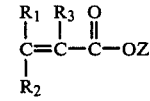

wherein $R_1$ and $R_2$ are independently hydrogen or alkyl groups having up to 6 carbon atoms, $R_3$ is hydrogen or methyl, and is an alkyl, hydroxyalkyl or alkoxyalkyl group having up to about 11 carbon atoms; and (3) from about 0.1 to about 10 mols of di-ethylenically unsaturated cross-linking agent selected from the group consisting of: divinyl esters of dicarboxylic acids, divinyl ethers, divinyl hydrocarbons, aliphatic diol diesters of α,β-ethylenically unsaturated carboxylic acids, and combinations thereof;

(b) forming a lens from said polymerized components;

(c) contacting said lens with a substantially water-free liquid alcohol having 3 to 7 carbon atoms in the presence of an acid catalyst for a time sufficient and under conditions to effect esterification;

(d) simultaneously with said esterification, removing aqueous distillate from said alcohol during said contact;

(e) contacting said esterified lens with methanol, ethanol, ether or a combination thereof for a time sufficient and under conditions to substantially extract from said esterified lens said 3 to 7 carbon atom alcohol which is unreacted; and (f) removing said methanol, ethanol, ether or combination thereof from said lens by evaporation.

27. The process of claim 26, wherein said polymerizable components comprise, per 100 mols of said polymerizable components, from about 20 to about 40 mols of said α,β-ethylenically unsaturated carboxylic acid, from about 60 to about 80 mols of said carboxylic acid ester, and from about 1 to about 3 mols of said cross-linking agent.

28. The process of claim 26, wherein said acid catalyst is sulfuric acid present in a concentration of from about 0.2 to about 5 percent by weight of said 3 to 7 carbon alcohol.

29. The process of claim 26, wherein said contact of said lens with said 3 to 7 carbon alcohol is at a temperature from about 50° C. to about 200° C. for a period of time from about 1 to about 100 hours.

30. The process of claim 26, wherein said contact of said esterified lens with said methanol, ethanol, ether or combination thereof is at a temperature from about 60° C. to about 80° C. for a period of time from about 4 to about 120 hours.

31. The process of claim 26, wherein said evaporation is at a temperature from up to about 80° C. for a period of time from about 8 to about 72 hours.

32. A process for making soft contact or intraocular lenses, comprising the steps of:

(a) polymerizing polymerizable components including, per 100 mols of each said components:

(1) from about 10 to about 90 mols of at least one monomer selected from the group consisting of α,β-ethylenically unsaturated carboxylic acids of the formula

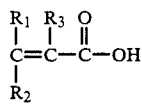

where $R_1$ and $R_2$ are independently hydrogen or alkyl groups having up to 6 carbon atoms and $R_3$ is hydrogen or methyl, said acid monomer being present in an amount sufficient for the resulting polymer to contain at least 10 weight percent of pendant carboxyl groups;

(2) from about 10 to about 90 mols of at least one monomer selected from the group consisting of esters of α,β-ethylenically unsaturated carboxylic acids having the formula

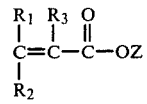

wherein $R_1$ and $R_2$ are independently hydrogen or alkyl groups having up to 6 carbon atoms, $R_3$ is hydrogen or methyl, and Z is an alkyl, hydroxyalkyl or alkoxyalkyl group having up to about 11 carbon atoms; and (3) from about 0.1 to about 10 mols of di-ethylenically unsaturated cross-linking agent selected from the group consisting of: divinyl esters of dicarboxylic acids, divinyl ethers, divinyl hydrocarbons, aliphatic diol diesters of α,β-ethylenically unsaturated carboxylic acids, and combinations thereof;

(b) forming a lens from said polymerized components;

(c) forming a peripheral bore in said lens;

(d) contacting said lens with a substantially water-free liquid alcohol having 3 to 7 carbon atoms at a temperature from about 50 to about 200° C. for a period of time from about 1 to about 100 hours in the presence of from about 0.2 to about 5 percent by weight of said alcohol of an acid catalyst to esterify said hard polymer;

(e) simultaneously with said esterification, removing aqueous distillate from said alcohol during said contact;

(f) contacting said esterified lens with liquid methanol, ethanol, ether or a combination thereof for a period of time from about 4 to about 120 hours at a temperature from about 20° C. to about 100° C. to substantially extract from said esterified lens said 3 to 7 carbon atom alcohol which is unreacted; and (g) inserting an end of a haptic into said peripheral bore, said haptic end having a portion of enlarged transverse cross-section; and (h) removing said methanol, ethanol, ether or combination thereof from said lens by evaporating said methanol, ethanol, ether or combination thereof at a temperature up to about 80° C. for a period of time from about 8 to about 72 hours, thereby contracting said lens, whereby said haptic is secured to said lens by contraction of said peripheral bore about said enlarged portion.

33. The process of claim 32, wherein said steps (a)-(d) and (f)-(h) are performed consecutively in the order in which said steps are set forth.

34. The process of claim 32, wherein said polymerizable components comprise, per 100 mols of said polymerizable components, from about 20 to about 40 mols of said α,β-ethylenically unsaturated carboxylic acid, from about 60 to about 80 mols of said carboxylic acid ester, and from about 1 to about 3 mols of said cross-linking agent.

35. The process of claim 32, wherein said contact of said lens with said 3 to 7 carbon atom alcohol is for a period of time from 10 to 20 hours.

36. The process of claim 32, wherein said contact of said esterified lens with said methanol, ethanol, ether or combination thereof is at a temperature from about 60° C. to about 80° C. for a period of time from about 36 to about 72 hours.

37. The process of claim 32, further comprising the steps of:

polishing said lens subsequent to said formation of said peripheral bore therein; and prior to said esterification, drying said polished lens at a temperature up to about 60° C. for a period of time from about 8 to about 72 hours.

* * * * *